US009687648B2

(12) United States Patent
Kulkarni et al.

(10) Patent No.: US 9,687,648 B2
(45) Date of Patent: Jun. 27, 2017

(54) SYSTEMS AND METHODS FOR POSITIONING AN INTRANEURAL ELECTRODE ARRAY IN AN AUDITORY NERVE

(71) Applicant: ADVANCED BIONICS AG, Staefa (CH)

(72) Inventors: Abhijit Kulkarni, Newbury Park, CA (US); Leonid M. Litvak, Los Angeles, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/022,559

(22) PCT Filed: Sep. 17, 2013

(86) PCT No.: PCT/US2013/060169
§ 371 (c)(1),
(2) Date: Mar. 16, 2016

(87) PCT Pub. No.: WO2015/041631
PCT Pub. Date: Mar. 26, 2015

(65) Prior Publication Data
US 2016/0228694 A1      Aug. 11, 2016

(51) Int. Cl.
*A61N 1/00* (2006.01)
*A61N 1/05* (2006.01)
(Continued)

(52) U.S. Cl.
CPC ........ *A61N 1/0541* (2013.01); *A61B 5/04845* (2013.01); *A61B 5/0538* (2013.01);
(Continued)

(58) Field of Classification Search
CPC A61N 1/0541; A61B 5/04845; A61B 5/0538; A61B 5/4851
See application file for complete search history.

(56) References Cited

U.S. PATENT DOCUMENTS 8,532,781 B1   9/2013   Vanpoucke
9,302,106 B2   4/2016   Kulkarni
(Continued)

FOREIGN PATENT DOCUMENTS

WO   WO-2007/092319   8/2007
WO   WO-2010/035149   4/2010

OTHER PUBLICATIONS

International Search Report and Written Opinion received in International Application No. PCT/US13/060169, dated Jan. 20, 2014.

*Primary Examiner* — Robert N Wieland
(74) *Attorney, Agent, or Firm* — ALG Intellectual Property, LLC

(57) ABSTRACT

An exemplary system may include an intracochlear electrode array configured to be inserted into a cochlea of a patient, an intraneural probe comprising an intraneural electrode contact and configured to be inserted into an auditory nerve of the patient, and a computing system. The computing system may be configured to identify an optimal insertion path for an intraneural electrode array into the auditory nerve of the patient by 1) repeatedly stimulating the intraneural electrode contact of the intraneural probe while the intraneural probe is advanced into the auditory nerve along a probe insertion path, 2) using the intracochlear electrode array to record a plurality of evoked responses that occur in response to the repeated stimulation of the intraneural electrode contact, and 3) determining, based on the plurality of evoked responses, whether the probe insertion path is the optimal insertion path for the intraneural electrode array.

21 Claims, 9 Drawing Sheets

(51) Int. Cl.
*A61B 5/00* (2006.01)
*A61B 5/0484* (2006.01)
*A61B 5/053* (2006.01)
*A61B 5/12* (2006.01)
*A61B 5/06* (2006.01)

(52) U.S. Cl.
CPC .............. *A61B 5/068* (2013.01); *A61B 5/12* (2013.01); *A61B 5/4851* (2013.01); *A61B 5/686* (2013.01); *A61B 5/6877* (2013.01); *A61B 5/061* (2013.01)

(56) References Cited

U.S. PATENT DOCUMENTS

| | | |
|---|---|---|
| 2004/0006264 A1 | 1/2004 | Mojarradi et al. |
| 2005/0004627 A1 | 1/2005 | Gibson |
| 2009/0143840 A1* | 6/2009 | Middlebrooks .... A61N 1/36032 607/57 |
| 2009/0254149 A1 | 10/2009 | Polak |

* cited by examiner

SYSTEMS AND METHODS FOR POSITIONING AN INTRANEURAL ELECTRODE ARRAY IN AN AUDITORY NERVE

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems have been developed. Cochlear implant systems bypass the hair cells in the cochlea by presenting electrical stimulation to the auditory nerve fibers by way of one or more channels formed by an array of electrodes implanted in the cochlea. Stimulation of the auditory nerve fibers leads to the perception of sound in the brain and at least partial restoration of hearing function.

Unfortunately, conventional cochlear implant systems cannot present a full spectrum of audible sound to the patient. For example, there are often sounds that have pitches lower than those which can be conventionally generated by applying electrical stimulation to one or more electrodes disposed within the cochlea of a patient. This is especially the case when ossification, malformations within the cochlea, and/or other anatomical anomalies prevent full insertion and/or function of an electrode lead within the cochlea.

Intraneural stimulation has been proposed as an alternative to intracochlear stimulation that may facilitate better representation of relatively low frequencies and finer spectral resolution throughout the entire hearing spectrum. In intraneural stimulation, an electrode array is inserted into the auditory nerve (e.g., at the base of the cochlea). Individual electrode contacts disposed on the electrode array may then be used to directly stimulate individual nerve fibers included in the auditory nerve, thereby allowing an intraneural stimulation system to convey a full spectrum of audible sound to the patient.

The nerve fibers within the auditory nerve are arranged in a helical fashion such that a transverse section of the auditory nerve will not represent a monotonic organization of pitch. Hence, an electrode array must be precisely positioned within the auditory nerve in order to gain access to the full spectrum of frequencies associated with the nerve fibers. Unfortunately, because the auditory nerve bundle itself cannot be visualized during surgery, the insertion trajectory of the electrode array cannot be guided. As a consequence, the electrode array can be easily placed in a position that misses gaining access to certain frequencies associated with the auditory nerve bundle.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for positioning an intraneural electrode array in an auditory nerve are described herein. As will be described below, an intraneural electrode array positioning system may include 1) an intracochlear electrode array configured to be inserted into a cochlea of a patient, 2) an intraneural probe comprising an intraneural electrode contact and configured to be inserted into an auditory nerve (also referred to as a cochlear nerve) of the patient, and 3) a computing system communicatively coupled to the intracochlear electrode array and the intraneural probe. The computing system may identify an optimal insertion path for an intraneural electrode array into the auditory nerve of the patient by repeatedly stimulating the intraneural electrode contact of the intraneural probe while the intraneural probe is advanced into the auditory nerve along a probe insertion path, using the intracochlear electrode array to record a plurality of evoked responses that occur in response to the repeated stimulation of the intraneural electrode contact, and determining, based on the plurality of evoked responses, whether the probe insertion path is the optimal insertion path for the intraneural electrode array. This process may be repeated for various probe insertion paths until an optimal insertion path is identified.

The systems and methods described herein may advantageously allow a user (e.g., a surgeon) to precisely insert an intraneural electrode array into the auditory nerve in a manner that allows the intraneural electrode array to have access to the full spectrum of frequencies associated with the nerve fibers included within the auditory nerve. The systems and methods described herein may also obviate the need to expose the auditory nerve during surgery in order to visualize the trajectory of the intraneural electrode array, which involves significant surgical risk resulting from opening the intra-meatal space. Other benefits of the systems and methods described herein will be described in more detail below.

Figure 1:
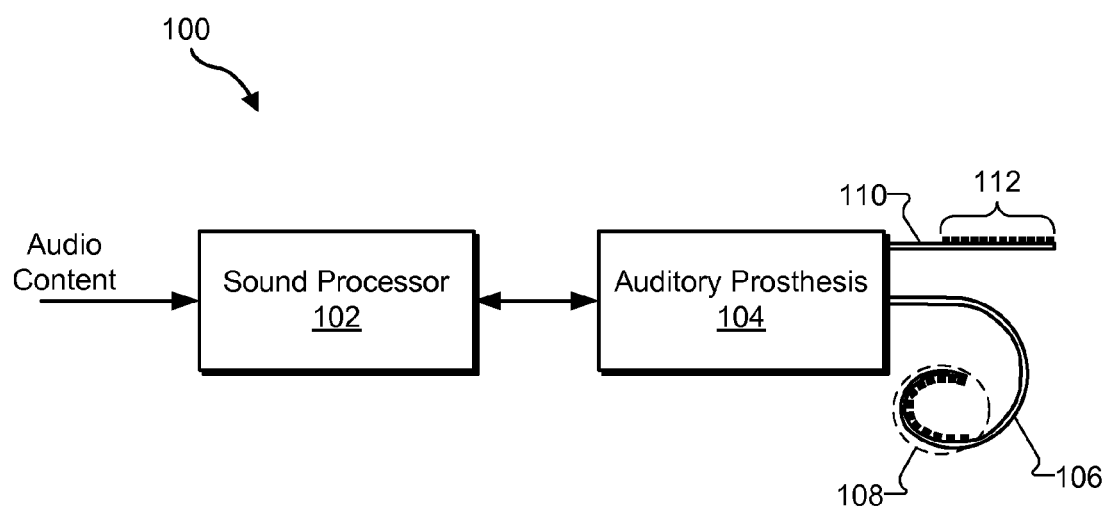
FIG. 1 illustrates an exemplary intraneural stimulation system according to principles described herein.

FIG. 1 illustrates an exemplary intraneural stimulation system 100. As shown, intraneural stimulation system 100 may include a sound processor 102, an auditory prosthesis 104, an intracochlear electrode array 106 (e.g., a lead) having a plurality of intracochlear electrode contacts 108 disposed thereon, and an intraneural electrode array 110 having a plurality of intraneural electrode contacts 112 disposed thereon.

Sound processor 102 may include any suitable device configured to process audio content (e.g., one or more audio signals) presented to a patient and direct auditory prosthesis 104 to apply electrical stimulation representative of the audio content to the auditory nerve of the patient by way of intracochlear electrode array 106 and/or intraneural electrode array 110 (i.e., by way of one or more intracochlear electrode contacts 108 and/or intraneural electrode contacts 112. Sound processor 102 may be implemented by a behind-the-ear ("BTE") unit, a body worn device, a portable speech processor ("PSP"), an electro-acoustic stimulation device ("EAS device"), and/or any other type of sound processing unit as may serve a particular implementation.

Auditory prosthesis 104 may include any suitable auditory prosthesis configured to be at least partially implanted within a patient as may serve a particular implementation. For example, auditory prosthesis 104 may include a cochlear implant, a brainstem implant and/or any other type of auditory prosthesis. Sound processor 102 and auditory prosthesis 104 may communicate by way of any suitable wired or wireless communication channel.

Intracochlear electrode array 106 may be may be inserted into the cochlea of the patient such that intracochlear electrode contacts 108 are in communication with stimulation sites within the cochlea. In this configuration, sound processor 102 may direct auditory prosthesis 104 to apply electrical stimulation representative of an audio signal to one or more stimulation sites within the cochlea by way of one or more of intracochlear electrode contacts 108. As used herein, the term "in communication with" refers to intracochlear electrode contacts 108 being adjacent to, in the general vicinity of, in close proximity to, directly next to, or directly on the one or more stimulation sites. Any number of intracochlear electrode contacts 108 may be disposed on intracochlear electrode array 106 as may serve a particular implementation.

Figure 2:
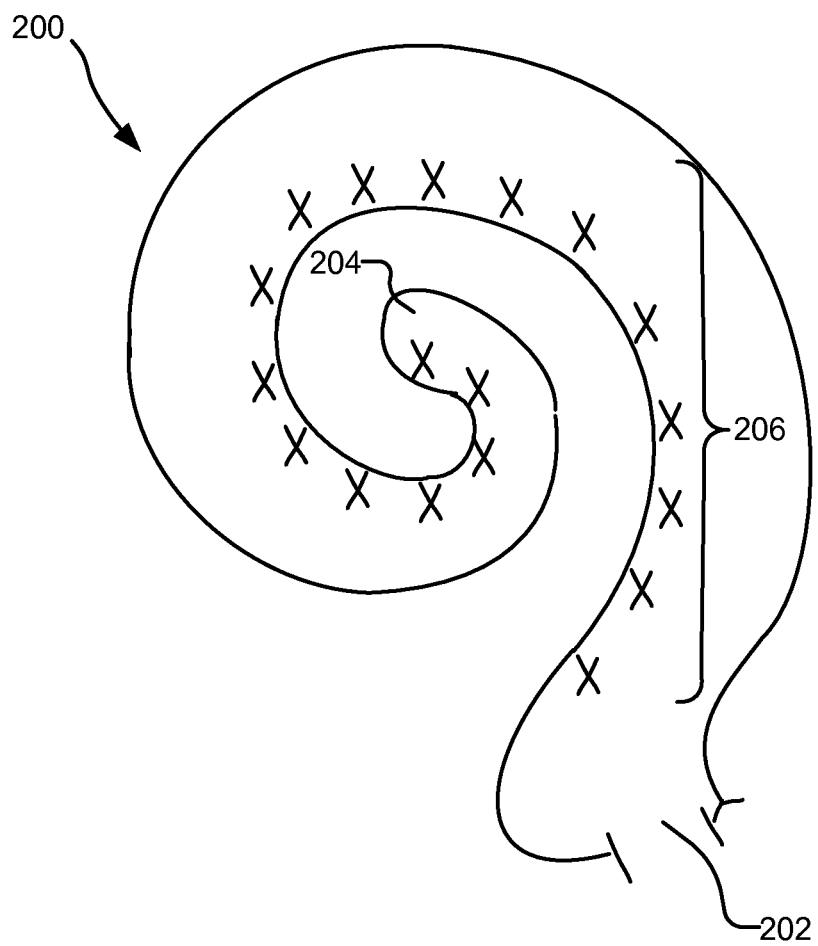
FIG. 2 illustrates a schematic structure of the human cochlea.

FIG. 2 illustrates a schematic structure of the human cochlea 200 into which intracochlear electrode array 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrode contacts disposed within the apical region (i.e., "apical electrode contacts") may result in the patient perceiving relatively low frequencies and electrical stimulation applied by way of electrode contacts disposed within the basal region (i.e., "basal electrode contacts") may result in the patient perceiving relatively high frequencies. The delineation between the apical and basal electrode contacts on a particular electrode lead may vary depending on the insertion depth of the lead, the anatomy of the patient's cochlea, and/or any other factor as may serve a particular implementation.

Returning to FIG. 1, intraneural electrode array 110 may be inserted into the auditory nerve of the patient such that intraneural electrode contacts 112 are in communication with various nerve fibers included within the auditory nerve. In this configuration, sound processor 102 may direct auditory prosthesis 104 to apply electrical stimulation representative of an audio signal directly to one or more nerve fibers included within the auditory nerve by way of one or more of intraneural electrode contacts 112. Any number of intraneural electrode contacts 112 may be disposed on intraneural electrode array 110 as may serve a particular implementation.

Figure 3:
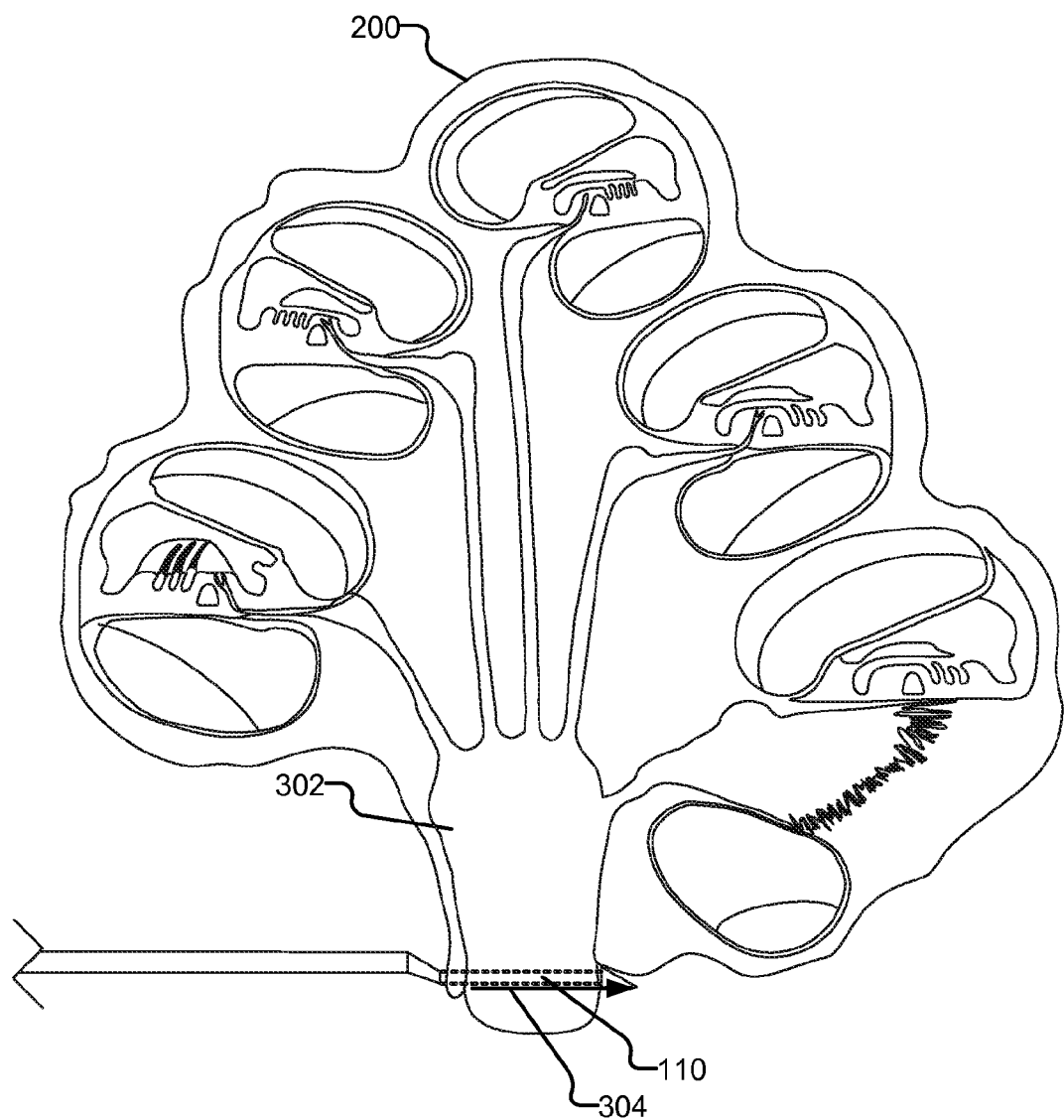
FIG. 3 illustrates an exemplary cross-sectional view of the human cochlea and the auditory nerve with an intraneural electrode array placed therein according to principles described herein.

To illustrate, FIG. 3 shows an exemplary cross-sectional view of human cochlea 200 and an auditory nerve 302. As shown, auditory nerve 302 exits cochlea 200 at a base of cochlea 200 and forms a nerve bundle, or trunk. In some examples, intraneural electrode array 110 may be inserted into the trunk of auditory nerve 302 along an insertion path 304, as shown by the arrow in FIG. 3. It will be recognized that intraneural electrode array 110 may be inserted into auditory nerve 302 at any other suitable location as may serve a particular implementation.

Figure 4:
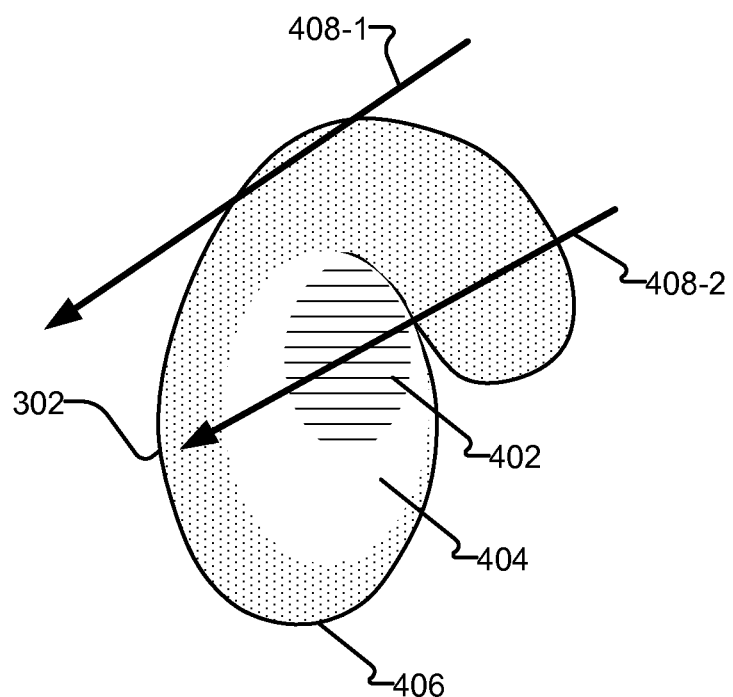
FIG. 4 illustrates an exemplary cross-sectional view of the human auditory nerve with different probe insertion paths illustrated according to principles described herein.

As mentioned, the nerve fibers within the auditory nerve are organized helically. To illustrate, FIG. 4 shows another exemplary cross-sectional view of auditory nerve 302. As shown, auditory nerve 302 may include low frequency nerve fibers 402 (i.e., nerve fibers configured to convey information included in a low frequency range to a person) located towards the core of auditory nerve 302, middle frequency nerve fibers 404 (i.e., nerve fibers configured to convey information included in a middle frequency range to a person) helically surrounding low frequency nerve fibers 402, and high frequency nerve fibers 406 (i.e., nerve fibers configured to convey information included in a high frequency range to a person) helically surrounding middle frequency nerve fibers 402. As used herein, a "low frequency range" refers to a set of relatively low frequencies (e.g., below 1000 Hz), a "high frequency range" refers to a set of relatively high frequencies (e.g., above 2000 Hz), and a middle frequency range refers to a set of frequencies in between the low and high frequency ranges (e.g., 1000 Hz to 2000 Hz). It will be recognized that the frequency boundaries between each frequency range may vary as may serve a particular implementation.

As described above, it is desirable for intraneural electrode array 110 to be in contact with each region of auditory nerve 302 (i.e., in contact with low frequency nerve fibers 402, middle frequency nerve fibers 404, and high frequency nerve fibers 406) in order for intraneural electrode array 110 to gain access to the full spectrum of frequencies associated with the nerve fibers included in auditory nerve 302. However, because of the helical nature of auditory nerve 302 and because auditory nerve 302 cannot be visualized during surgery, it is possible for intraneural electrode array 110 to be inserted or advanced into auditory nerve 302 along an insertion path that misses (or makes minimal contact with) low frequency nerve fibers 402, middle frequency nerve fibers 404, and/or high frequency nerve fibers 406.

To illustrate, FIG. 4 shows two possible insertion paths 408-1 and 408-2 along which intraneural electrode array 110 may be advanced into auditory nerve 302. As shown, insertion path 408-1 barely glances auditory nerve 302 and, as a result, only makes contact with high frequency nerve fibers 406 (and not with low frequency nerve fibers 402 and middle frequency nerve fibers 404). On the other hand, insertion path 408-2 makes contact with low frequency nerve fibers 402, middle frequency nerve fibers 404, and high frequency nerve fibers 406, and hence is preferable to insertion path 408-1. As shown, insertion path 408-2 follows a substantially linear trajectory. It will be recognized that the possible insertion paths through auditory nerve 302 are infinite and are not limited to those specifically illustrated in FIG. 4.

Figure 5:
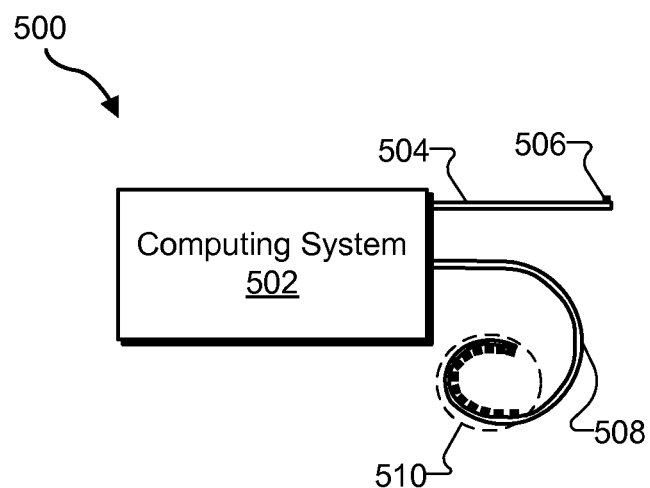
FIG. 5 illustrates an exemplary intraneural electrode array positioning system according to principles described herein.

FIG. 5 illustrates an exemplary intraneural electrode array positioning system 500 (or simply "system 500") that may be used to correctly position an intraneural electrode array (e.g., intraneural electrode array 110) within an auditory nerve (e.g., auditory nerve 302). In other words, system 500 may be used to position an intraneural electrode array within an auditory nerve in a manner that results in the intraneural electrode array being in contact with low frequency nerve fibers, middle frequency nerve fibers, and high frequency nerve fibers.

As shown, intraneural electrode array positioning system 500 may include a computing system 502 communicatively coupled to an intraneural probe 504 having an intraneural electrode contact 506 disposed thereon and to an intracochlear electrode array 508 having a plurality of intracochlear electrode contacts 510 disposed thereon. A single intraneural electrode contact 506 is shown in FIG. 5 for illustrative purposes only. It will be recognized that in some alternative embodiments, intraneural probe 504 may have a plurality of intraneural electrode contacts disposed thereon. For example, the intraneural electrode array itself may be used as the intraneural probe 504. However, for purposes of the examples provided herein, it will be assumed that intraneural probe 504 is separate from the intraneural electrode array and that intraneural probe 504 has a single intraneural electrode contact 506 disposed thereon.

Intraneural probe 504 may be used to determine an optimal insertion path for an intraneural electrode array into an auditory nerve. For example, as will be described below, intraneural probe 504 may be repeatedly inserted into the auditory nerve along a plurality of different probe insertion paths until computing system 504 determines that a particular probe insertion path is optimal (i.e., that the trajectory of the probe insertion path is such that an intraneural electrode array inserted into the auditory nerve along the particular probe insertion path will be in contact with low frequency nerve fibers, middle frequency nerve fibers, and high frequency nerve fibers).

Intracochlear electrode array 508 may be implemented by any suitable lead that may be inserted to the cochlea of a patient. For example, intracochlear electrode array 508 may be implemented by intracochlear electrode array 106. In this implementation, intracochlear electrode array 508 may be communicatively coupled to computing system 502 by way of auditory prosthesis 104 and sound processor 102. For example, computing system 502 may be coupled to sound processor 102. In this configuration, computing system 502 may use intracochlear electrode contacts 510 to record evoked responses that occur in response to stimulation of intraneural electrode contact 506 by receiving recording data acquired by intracochlear electrode contacts 510 by way of sound processor 102. Alternatively, intracochlear electrode array 508 may be communicatively coupled directly to computing system 502. For example, intracochlear electrode array 508 may be coupled to computing system 502 during an implantation procedure in which intracochlear electrode array 508 is implanted within the patient. Once computing system 502 has used intracochlear electrode array 508 to determine the optimal insertion path for the intraneural electrode array, intracochlear electrode array 508 may be disconnected from computing system 502 and connected to auditory prosthesis 104.

Computing system 502 may be configured to identify an optimal insertion path for an intraneural electrode array into the auditory nerve. To this end, computing system 502 may be implemented by any suitable combination of computing and communication devices including, but not limited to, a fitting device, a personal computer, a laptop computer, a handheld device, a mobile device (e.g., a mobile phone), and/or any other suitable component as may serve a particular implementation. In some examples, computing system 502 may provide one or more graphical user interfaces ("GUIs") with which a clinician or other user may interface in order to determine the optimal insertion path.

Figure 6:
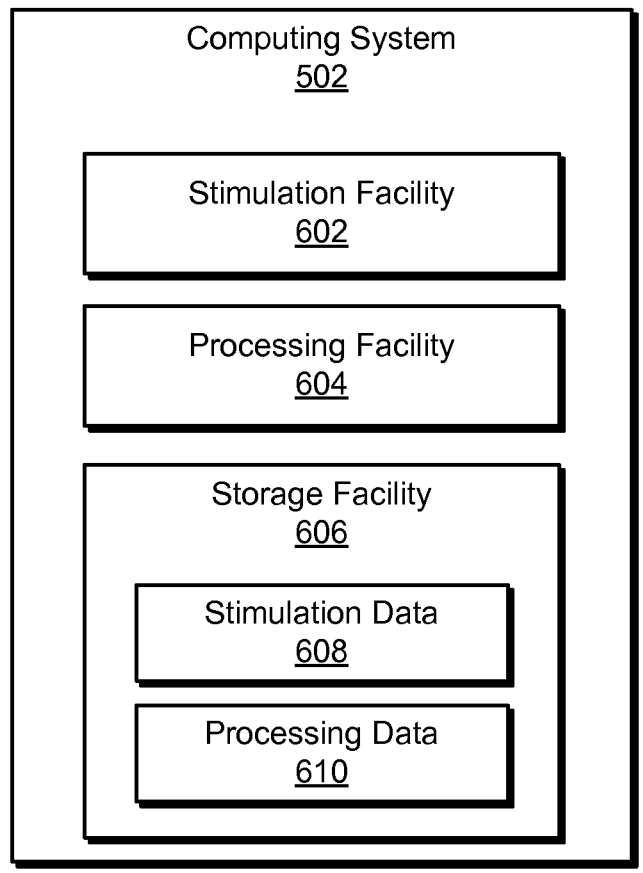
FIG. 6 illustrates exemplary components of a computing system according to principles described herein.

FIG. 6 illustrates exemplary components of computing system 502. As shown in FIG. 6, computing system 502 may include a stimulation facility 602, a processing facility 604, and a storage facility 606, which may be in communication with one another using any suitable communication technologies. Storage facility 606 may maintain stimulation data 608 generated and/or used by stimulation facility 602 and processing data 610 generated and/or used by processing facility 604. Storage facility 606 may maintain additional or alternative data as may serve a particular implementation.

Stimulation facility 602 may be configured to perform one or more stimulation operations. For example, as intraneural probe 504 is advanced (e.g., by a surgeon or other user) into the auditory nerve of a patient along a probe insertion path, stimulation facility 602 may repeatedly stimulate intraneural electrode contact 506. This may be performed in any suitable manner. For example, stimulation facility 602 may generate and provide electrical stimulation current by way of intraneural electrode contact 506. The electrical stimulation current may have any suitable characteristic (e.g., amplitude, duration, frequency, etc.) as may serve a particular implementation.

The frequency at which stimulation facility 602 repeatedly stimulates intraneural electrode contact 506 as intraneural probe 504 is advanced into the auditory nerve of a patient along the probe insertion path may vary as may serve a particular implementation. For example, a user may advance intraneural probe 504 along the probe insertion path an incremental distance and then stop. While intraneural probe 504 is stationary, stimulation facility 602 may stimulate intraneural electrode contact 506. The user may then advance intraneural probe 504 another incremental distance and then stop. While intraneural probe 504 is again stationary, stimulation facility 602 may again stimulate intraneural electrode contact 506. This process may be repeated any suitable number of times as may serve a particular implementation. Alternatively, stimulation facility 602 may repeatedly stimulate intraneural electrode contact 506 while intraneural probe 504 is continuously advanced along the probe insertion path.

Processing facility 604 may be configured to use intracochlear electrode array 508 (e.g., one or more of intracochlear electrode contacts 510) to record a plurality of evoked responses that occur in response to the repeated stimulation of intraneural electrode contact 506 while intraneural probe 504 is advanced into the auditory nerve along the probe insertion path. As used herein, an "evoked response" refers to a neural response (e.g., a compound action potential) and/or any other type of physiological response that may occur within a patient in response to application of electrical stimulation by way of intraneural electrode contact 506.

Processing facility 604 may be further configured to determine, based on the plurality of evoked responses, whether the probe insertion path is an optimal insertion path for the intraneural electrode array. This may be performed in any suitable manner. For example, processing facility 604 may determine that the probe insertion path is an optimal insertion path for the intraneural electrode array if the evoked responses represent an excitation of the auditory nerve above a predetermined excitation threshold in each of a high frequency range, a middle frequency range, and a low frequency range.

Figure 7:
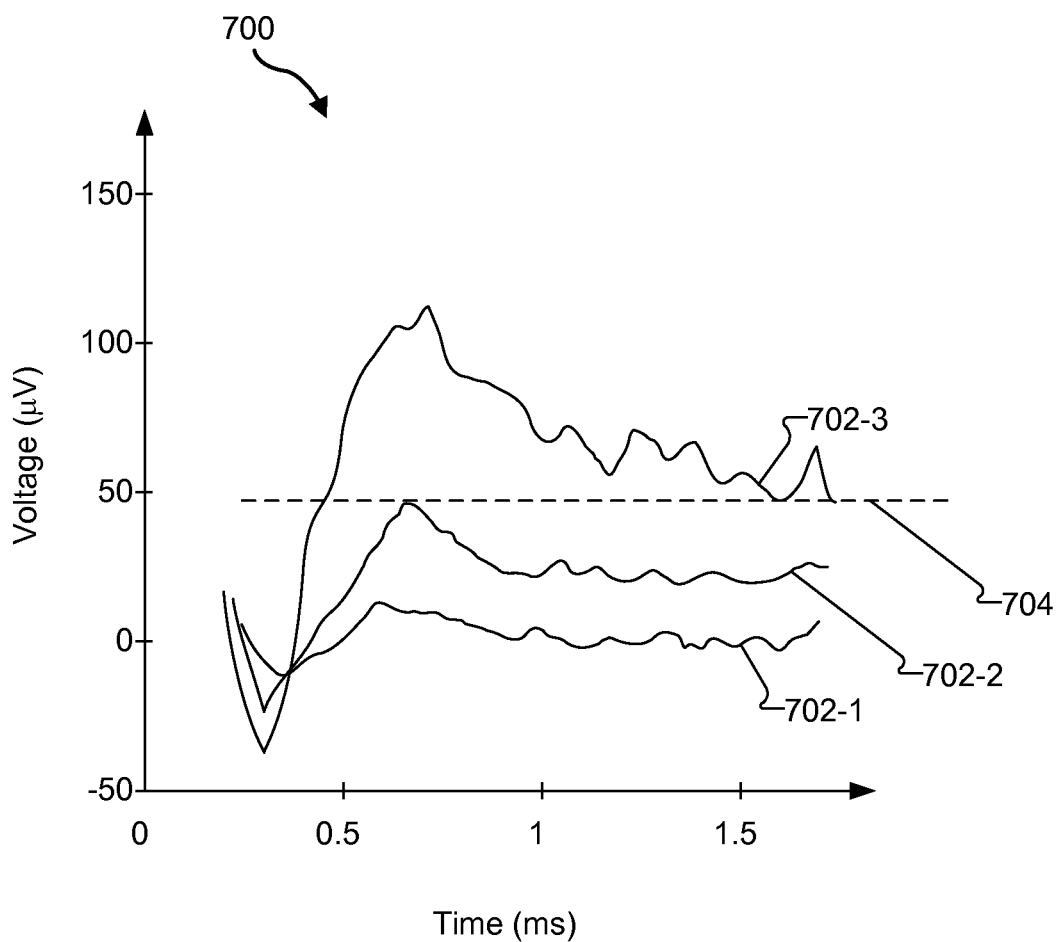
FIG. 7 illustrates a graph of evoked responses according to the principles described herein.

To illustrate, FIG. 7 shows a graph 700 of evoked responses 702 (e.g., evoked responses 702-1 through 702-3) that may be recorded by an intracochlear electrode contact 510 in response to stimulation of intraneural electrode contact 506. As shown, each evoked response 702 may have a steady-state amplitude that is either above or below a predetermined threshold 704. For example, evoked responses 702-1 and 702-2 have a steady-state amplitude below predetermined threshold 704 and evoked response 702-3 has a steady-state amplitude above predetermined threshold 704.

In some examples, predetermined threshold 704 may correspond to the predetermined excitation threshold. In other words, if an evoked response has a steady-state amplitude that is greater than predetermined threshold 704, the evoked response indicates that nerve fibers located in the proximity of the intracochlear electrode contact 510 that recorded the evoked response have been excited by the stimulation of intraneural electrode contact 506. By identifying which intracochlear electrode contact 510 recorded the evoked response, processing facility 604 may determine which nerve fibers (i.e., low frequency nerve fibers, middle frequency nerve fibers, or high frequency nerve fibers) were stimulated by intraneural electrode contact 506.

To illustrate, a clinician may advance intraneural probe 504 along probe insertion path 408-1 shown in FIG. 4. While intraneural probe 504 is advanced, stimulation facility 602 may repeatedly stimulate intraneural electrode contact 506. Processing facility 604 may determine that only those intracochlear electrode contacts 510 located in a high frequency region of the cochlea record evoked responses that have amplitudes above predetermined threshold 704. All other intracochlear electrode contacts 510 (i.e., intracochlear electrode contacts 510 located in the low and middle frequency regions of the cochlea) either do not produce evoked responses or produce evoked responses that have amplitudes below predetermined threshold 704. Hence, processing facility 604 may determine that probe insertion path 408-1 only results in excitation of high frequency nerve fibers 406 and that it therefore is not an optimal insertion path for the intraneural electrode array.

Based on this information, the clinician may remove intraneural probe 504 and advance intraneural probe 504 along probe insertion path 408-2 shown in FIG. 4. While intraneural probe 504 is advanced, stimulation facility 602 may repeatedly stimulate intraneural electrode contact 506. Processing facility 604 may first determine that intracochlear electrode contacts 510 located in a high frequency region of the cochlea record evoked responses that have amplitudes above predetermined threshold 704. As intraneural probe 504 is advanced further along probe insertion path 408-2, processing facility 604 may next determine that intracochlear electrode contacts 510 located in a low frequency region of the cochlea record evoked responses that have amplitudes above predetermined threshold 704. As intraneural probe 504 is advanced even further along probe insertion path 408-2, processing facility 604 may next determine that intracochlear electrode contacts 510 located in a middle frequency region of the cochlea record evoked responses that have amplitudes above predetermined threshold 704. Finally, as intraneural probe 504 is advanced even further along probe insertion path 408-2, processing facility 604 may again determine that intracochlear electrode contacts 510 located in the high frequency region of the cochlea record evoked responses that have amplitudes above predetermined threshold 704. Processing facility 604 may accordingly determine that probe insertion path 408-2 is an optimal insertion path for the intraneural electrode array. In this manner, the optional insertion path may be determined in real-time as intraneural probe 504 is advanced into the auditory nerve.

In some examples, processing facility 604 may present one or more graphical user interfaces ("GUIs") that may be utilized by a user (e.g., a surgeon) to determine whether a particular probe insertion path is an optimal insertion path for the intraneural electrode array. For example, processing facility 604 may present a GUI that displays a graph of evoked responses (e.g., graph 700) recorded by one or more intracochlear electrode contacts 510. In this manner, the user may visually determine whether a particular probe insertion path is an optimal insertion path for the intraneural electrode array. Additional or alternative information may be presented by way of the one or more GUIs as may serve a particular implementation.

Once an optimal insertion path for the intraneural electrode array has been determined, intraneural probe 504 may be removed from the auditory nerve and the intraneural electrode array may be advanced into the auditory nerve along the optimal insertion path. To this end, intraneural electrode array positioning system 500 may further include a stereotaxic apparatus that may be used to assist in inserting intraneural probe 504 and/or the intraneural electrode array into the auditory nerve along the optimal insertion path. In some examples, the stereotaxic apparatus may be configured to make use of a three-dimensional coordinate system to ensure proper insertion of intraneural probe 504 and/or the intraneural electrode array. The three-dimensional coordinate system may be established through head-holding clamps and/or bars, which put the patient's head in a fixed position in reference to the coordinate system. With the three-dimensional coordinate system, the intraneural electrode array may be accurately advanced along the optimal insertion path.

Processing facility 604 may be configured to perform one or more other operations associated with inserting intraneural probe 504 into the auditory nerve. For example, processing facility 604 may determine whether intraneural probe 504 has reached the auditory nerve by measuring an impedance of tissue along the probe insertion path with intraneural electrode contact 506 (and/or with any other sensor disposed on intraneural probe 504). This is because the impedance of tissue surrounding the auditory nerve 302 is different than the impedance of the auditory nerve itself. Hence, when processing facility 604 detects a change in impedance above a predetermined amount, processing facility 604 may determine that intraneural probe 504 has reached the auditory nerve.

Processing facility 604 may additionally or alternatively determine whether intraneural probe 504 has reached the auditory nerve by measuring an auditory brainstem response with an additional intraneural electrode contact disposed on intraneural probe 504. The auditory brainstem response may be measured in response to stimulation of intraneural electrode contact 506. If intraneural probe 504 has not reached the auditory nerve, the additional intraneural electrode contact will not detect an auditory brainstem response. However, if intraneural probe 504 has reached the auditory nerve, the additional intraneural electrode contact will detect an auditory brainstem response. Hence, the presence of an auditory brainstem response may allow processing facility 604 to determine that intraneural probe 504 has reached the auditory nerve.

Figure 8:
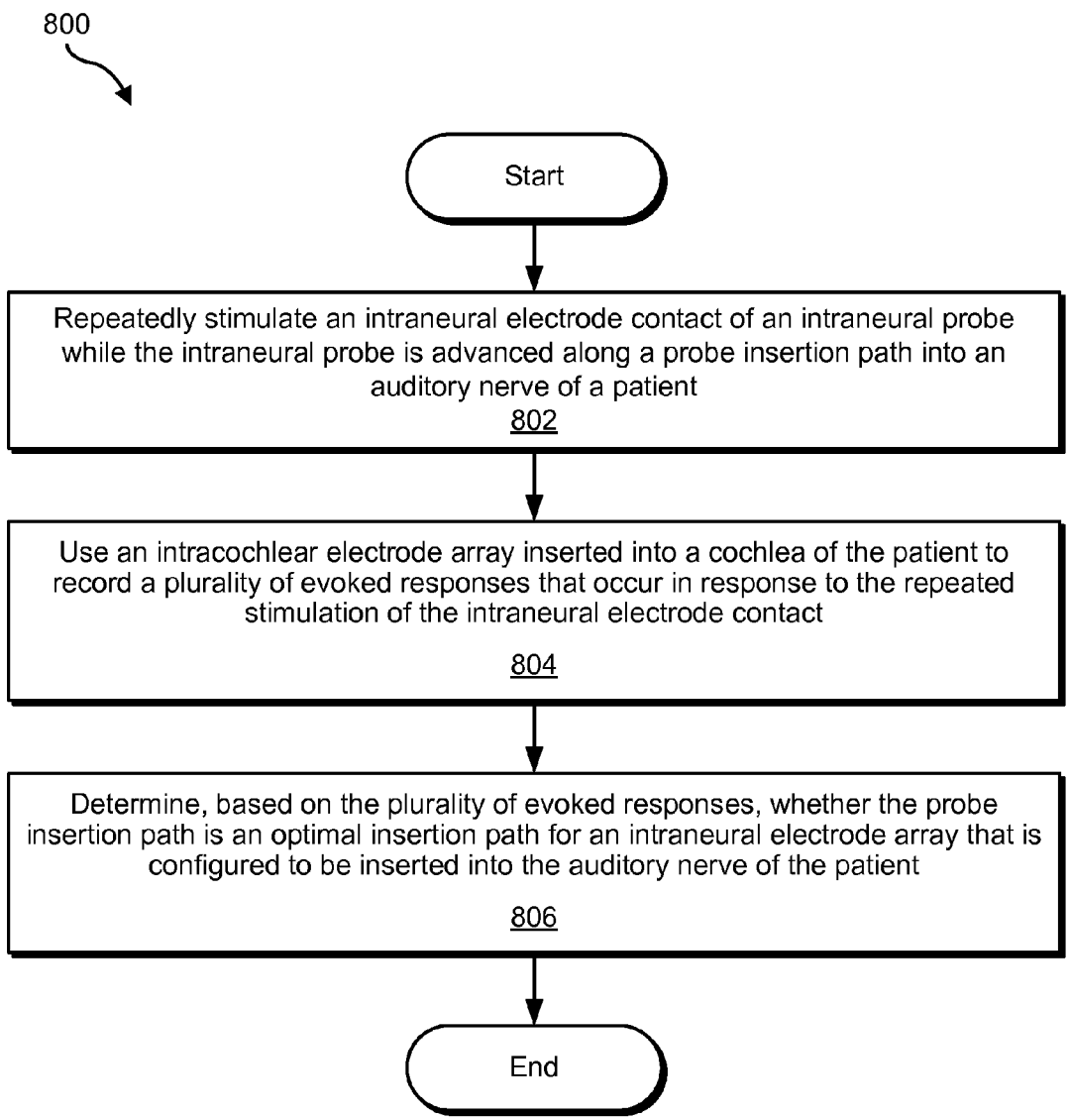
FIG. 8 illustrates an exemplary method of positioning an intraneural electrode array in an auditory nerve according to principles described herein.

FIG. 8 illustrates an exemplary method 800 of positioning an intraneural electrode array in an auditory nerve. While FIG. 8 illustrates exemplary steps according to one embodiment, other embodiments may omit, add to, reorder, and/or modify any of the steps shown in FIG. 8. One or more of the steps shown in FIG. 8 may be performed by computing system 502 and/or any implementation thereof.

In step 802, a computing system repeatedly stimulates an intraneural electrode contact of an intraneural probe while the intraneural probe is advanced along a probe insertion path into an auditory nerve of a patient. Step 802 may be performed in any of the ways described herein.

In step 804, the computing system uses an intracochlear electrode array inserted into a cochlea of the patient to record a plurality of evoked responses that occur in response to the repeated stimulation of the intraneural electrode contact. Step 804 may be performed in any of the ways described herein.

In step 806, the computing system determines, based on the plurality of evoked responses, whether the probe insertion path is an optimal insertion path for an intraneural electrode array that is configured to be inserted into the auditory nerve of the patient. Step 806 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 9:
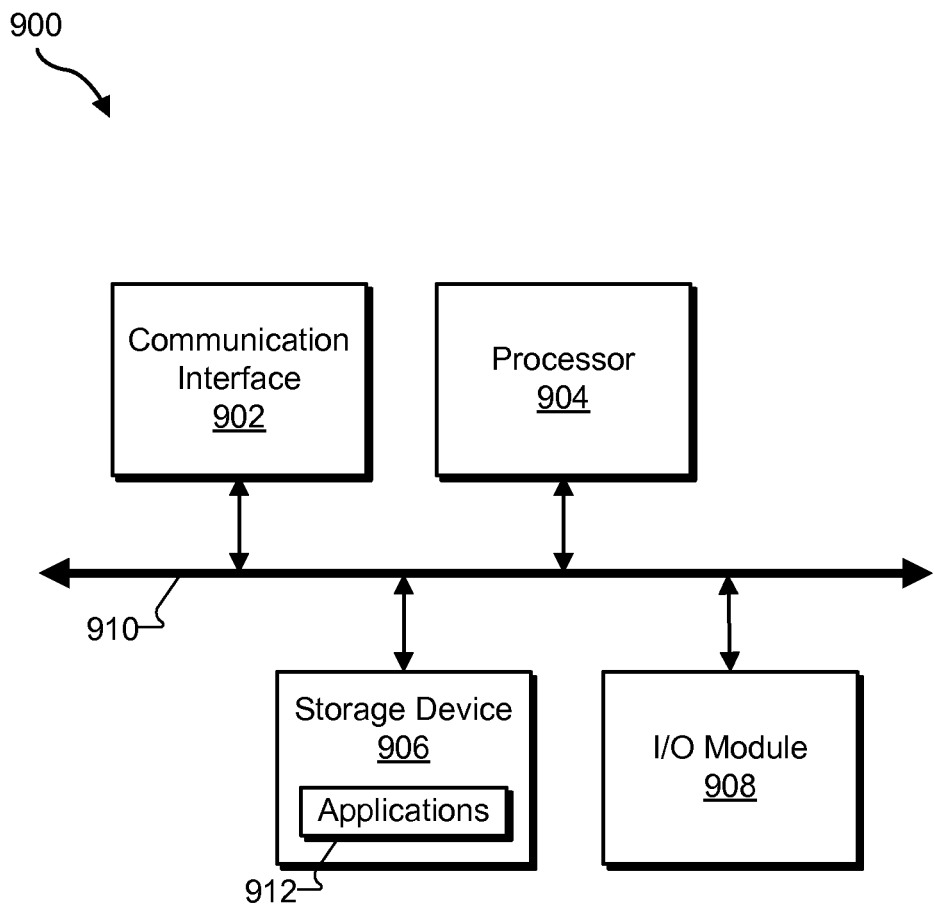
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 900. For example, one or more applications 912 residing within storage device 906 may be configured to direct processor 904 to perform one or more processes or functions associated with any of the facilities and/or systems described herein (e.g., stimulation facility 602 and/or processing facility 604).

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
an intracochlear electrode array configured to be inserted into a cochlea of a patient;
an intraneural probe comprising an intraneural electrode contact and configured to be inserted into an auditory nerve of the patient; and
a computing system communicatively coupled to the intracochlear electrode array and to the intraneural probe and configured to identify an optimal insertion path for an intraneural electrode array into the auditory nerve of the patient by
repeatedly stimulating the intraneural electrode contact of the intraneural probe while the intraneural probe is advanced into the auditory nerve along a probe insertion path,
using the intracochlear electrode array to record a plurality of evoked responses that occur in response to the repeated stimulation of the intraneural electrode contact, and
determining, based on the plurality of evoked responses, whether the probe insertion path is the optimal insertion path for the intraneural electrode array.

2. The system of claim 1, wherein if the evoked responses represent an excitation of the auditory nerve above a predetermined excitation threshold in each of a low frequency range, a middle frequency range, and a high frequency range, the computing system determines that the probe insertion path is the optimal insertion path for the intraneural electrode array.

3. The system of claim 2, wherein the computing system is configured to determine that the evoked responses represent an excitation of the auditory nerve above the predetermined excitation threshold in each of the low frequency range, the middle frequency range, and the high frequency range by:
determining that one or more intracochlear electrode contacts disposed on the intracochlear electrode array and located in a low frequency region of a cochlea of the patient record one or more evoked responses that have an amplitude above a predetermined threshold in response to the repeated stimulation of the intraneural electrode contact;
determining that one or more intracochlear electrode contacts disposed on the intracochlear electrode array and located in a middle frequency region of the cochlea of the patient record one or more evoked responses that have an amplitude above the predetermined threshold in response to the repeated stimulation of the intraneural electrode contact; and
determining that one or more intracochlear electrode contacts disposed on the intracochlear electrode array and located in a high frequency region of the cochlea of the patient record one or more evoked responses that have an amplitude above the predetermined threshold in response to the repeated stimulation of the intraneural electrode contact.

4. The system of claim 1, wherein the computing system is further configured to determine whether the intraneural probe has reached the auditory nerve by measuring an impedance of tissue along the probe insertion path with the intraneural electrode contact.

5. The system of claim 1, wherein the intraneural probe comprises an additional intraneural electrode contact, and wherein the computing system is further configured to determine whether the intraneural probe has reached the auditory nerve by measuring an auditory brainstem response with the additional intraneural electrode contact.

6. The system of claim 1, wherein the intraneural probe is the intraneural electrode array.

7. The system of claim 1, further comprising a stereotaxic apparatus configured to assist in inserting the intraneural probe along the probe insertion path.

8. The system of claim 1, wherein the optimal insertion path follows a linear trajectory.

9. The system of the claim 1, wherein if the evoked responses represent an excitation of the auditory nerve above a predetermined excitation threshold in each frequency range included in a plurality of frequency ranges, the computing system determines that the probe insertion path is the optimal insertion path for the intraneural electrode array.

10. A system comprising:
a stimulation facility configured to repeatedly stimulate an intraneural electrode contact of an intraneural probe while the intraneural probe is advanced along a probe insertion path into an auditory nerve of a patient; and
a processing facility communicatively coupled to the stimulation facility and configured to
use an intracochlear electrode array inserted into a cochlea of the patient to record a plurality of evoked responses that occur in response to the repeated stimulation of the intraneural electrode contact; and
determine, based on the plurality of evoked responses, whether the probe insertion path is an optimal insertion path for an intraneural electrode array that is configured to be inserted into the auditory nerve of the patient.

11. The system of claim 10, wherein if the evoked responses represent an excitation of the auditory nerve above a predetermined excitation threshold in each of a low frequency range, a middle frequency range, and a high frequency range, the processing facility determines that the probe insertion path is the optimal insertion path for the intraneural electrode array.

12. The system of claim 10, wherein the processing facility is further configured to determine whether the intraneural probe has reached the auditory nerve by measuring an impedance of tissue along the probe insertion path with the intraneural electrode contact.

13. The system of claim 10, wherein the intraneural probe comprises an additional intraneural electrode contact, and wherein the processing facility is further configured to determine whether the intraneural probe has reached the auditory nerve by measuring an auditory brainstem response with the additional intraneural electrode contact.

14. The system of claim 10, wherein the intraneural probe is the intraneural electrode array.

15. The system of claim 10, further comprising a stereotaxic apparatus configured to assist in inserting the intraneural probe along the probe insertion path.

16. A method comprising:
repeatedly stimulating, by a computing system, an intraneural electrode contact of an intraneural probe while the intraneural probe is advanced along a probe insertion path into an auditory nerve of a patient;
using, by the computing system, an intracochlear electrode array inserted into a cochlea of the patient to record a plurality of evoked responses that occur in response to the repeated stimulation of the intraneural electrode contact; and
determining, by the computing system and based on the plurality of evoked responses, whether the probe insertion path is an optimal insertion path for an intraneural electrode array that is configured to be inserted into the auditory nerve of the patient.

17. The method of claim 16, further comprising determining, by the computing system, that the probe insertion path is the optimal insertion path for the intraneural electrode array if the evoked responses represent an excitation of the auditory nerve above a predetermined excitation threshold in each of a low frequency range, a middle frequency range, and a high frequency range.

18. The method of claim 16, further comprising determining, by the computing system, whether the intraneural probe has reached the auditory nerve by measuring an impedance of tissue along the probe insertion path with the intraneural electrode contact.

19. The method of claim 16, further comprising determining, by the computing system, whether the intraneural probe has reached the auditory nerve by measuring an auditory brainstem response with an additional intraneural electrode contact provided on the intraneural probe.

20. The method of claim 16, wherein the intraneural probe is the intraneural electrode array.

21. The method of claim 16, further comprising using a stereotaxic apparatus to assist in inserting the intraneural probe along the probe insertion path.

* * * * *